(12) United States Patent
Hurley et al.

(10) Patent No.: US 7,968,533 B2
(45) Date of Patent: Jun. 28, 2011

(54) ETHYL NITRITE AS A GASTROINTESTINAL SMOOTH MUSCLE RELAXANT AND DIAGNOSTIC AND THERAPEUTIC USES THEREOF

(75) Inventors: Kevin P. Hurley, Chapel Hill, NC (US); Jonathan S. Stamler, Chapel Hill, NC (US); John Baillie, Durham, NC (US); James D. Reynolds, Durham, NC (US); Stephen O. Vaughan, Chapel Hill, NC (US)

(73) Assignee: Duke University, Durham, NC (US)

( * ) Notice: Subject to any disclaimer, the term of this patent is extended or adjusted under 35 U.S.C. 154(b) by 257 days.

(21) Appl. No.: 11/715,594

(22) Filed: Mar. 7, 2007

(65) Prior Publication Data

US 2008/0058425 A1  Mar. 6, 2008

Related U.S. Application Data (60) Provisional application No. 60/780,311, filed on Mar. 7, 2006.

(51) Int. Cl.
*A01N 43/00* (2006.01)
*A61K 31/33* (2006.01)

(52) U.S. Cl. ........................................ 514/183; 514/645
(58) Field of Classification Search .................. 514/183, 514/645
See application file for complete search history.

(56) References Cited

U.S. PATENT DOCUMENTS 6,488,951 B2 * 12/2002 Toone et al. .................. 424/423

FOREIGN PATENT DOCUMENTS

| WO | WO 01/17596 A1 | 3/2001 |
| WO | WO 03/011384 A1 | 2/2003 |
| WO | WO 03/041713 A1 | 5/2003 |

OTHER PUBLICATIONS

Furchgott, R.F. et al., "Comparison of Properties of Nitric Oxide and Endothelium-Derived Relaxing Factor: Some Cautionary Findings", *I. Endothelium-Derived Relaxing Factors and Nitric Oxide*, Rubanyi GM, Vanhoutte PM (eds.), Basel, Karger, pp. 8-21 (1990).
Gryglewski, R.J. et al., "Sperotide Anion is Involved in the Breakdown of Endothelium-Derived Vascular Relaxing Factor", *Nature*, 320(3):454-456 (1986).
Ignarro et al., "Endothelium-Derived Relaxing Factor Produced and Released from Artery and Vein is Nitric Oxide", *Proc. Natl. Acad. Sci. USA*, 84:9265-9269 (1987).
Ignarro, L.J., "Biological Action and Properties of Endothelium-Derived Nitric Oxide Formed and Released From Artery and Vein", *Circ. Res.*, 65(1):1-21 (1989).
Lancaster et al., "EPR Demonstration of Iron-Nitrosyl Complex Formation by Cytotoxic Activated Macrophages", *Proc. Natl. Acad. Sci. USA*, 87:1223-1227 (1990).
Organic Syntheses, Coll. vol. 2, A H Blatt ed, pp. 204-205 (1943).
Palmer et al., "Nitric Oxide Release Accounts for the Biological Activity of Endothelium-Derived Relaxing Factor", *Nature*, 327:524-526 (1987).

* cited by examiner

*Primary Examiner* — Brandon J Fetterolf
*Assistant Examiner* — Jean Cornet
(74) *Attorney, Agent, or Firm* — Mintz Levin Cohn Ferris Glovsky and Popeo, P.C.; Ivor R. Elrifi; Matthew Pavao (57) ABSTRACT

The present invention provides compositions comprising a gas and a gastrointestinal smooth muscle relaxing agent comprising ethyl nitrite in a therapeutically effective amount. The present invention also provides methods of relaxing gastrointestinal smooth muscle, alleviating contraction or spasm of gastrointestinal smooth muscle to facilitate a diagnostic medical procedure and treating or preventing a gastrointestinal disorder using the compositions of the invention.

20 Claims, 5 Drawing Sheets

T+1 min

ETHYL NITRITE
25 ppm

T+8 min

Fig. 3

ETHYL NITRITE 75 ppm

T +1 min

T +6 min

ETHYL NITRITE AS A GASTROINTESTINAL SMOOTH MUSCLE RELAXANT AND DIAGNOSTIC AND THERAPEUTIC USES THEREOF

RELATED APPLICATIONS

This application claims the benefit of U.S. Provisional Application No. 60/780,311, filed Mar. 7, 2006, the contents of which are incorporated herein by reference in its entirety.

FIELD OF THE INVENTION

The present invention is directed compositions comprising a gas and a gastrointestinal smooth muscle relaxing agent comprising ethyl nitrite in a therapeutically effective amount and methods of utilizing these compositions to relax gastrointestinal smooth muscle.

BACKGROUND

The endothelium secretes a vascular relaxing factor, known as endothelium-derived relaxing factor (EDRF), which has been identified as nitric oxide (NO), or a closely related derivative thereof. (Palmer et al., Nature 327:524-526 (1987); Ignarro et al., Proc. Natl. Acad. Sci. USA 84:9265-9269 (1987)). Under physiologic conditions, however, NO is exceedingly unstable, reacting essentially instantaneously with oxygen, superoxide anion, and redox metals (Lancaster et al., Proc. Natl. Acad. Sci. USA 87:1223-1227 (1990); Ignarro et al., Circ. Res. 65:1-21 (1989); and Gryglewski et al., Nature 320:454-456 (1986)). This fact has lead to the supposition that, in order to exert its effect on smooth muscle, NO must be stabilized in vivo in a form that preserves its biological activity.

Introduction of NO into biological tissue can also result in significant adverse effects, which occur as a direct result of the particular chemical reactivity of the uncharged NO radical (NO.). These adverse effects create impediments to NO therapy which generally involves administration of NO. For example, the reaction between NO., and $O_2$ or reactive $O_2$ species which are present in high concentrations in many tissues, generates highly toxic products, such as $NO_2$ and peroxynitrite. These reactions also result in the rapid inactivation of NO, thus eliminating any beneficial pharmacological effect. (Furchgott R. F. et al., I. Endothelium-Derived Relaxing Factors and Nitric Oxide; eds. Rubanyi G. M., pp. 8-21 (1990); Gryglewski, R. J. et al., Nature 320:454-456 (1986)).

Gastrointestinal smooth muscle has a vital role in the physiological function of the body. For example, in the gastrointestinal tract, the sphincter of Oddi, a valve between the duodenum and bile duct, provides tonic contraction which serves to prevent reflux of duodenal contents into the pancreatic and bile ducts, and promotes filling of the gall bladder. Moreover, a variety of significant clinical disorders occur, which involve contraction, spasm, or failure to achieve the necessary relaxation of gastrointestinal smooth muscle. Examples of such disorders include irritable bowel syndrome, achalasia, dumping disorders, etc. Thus, a clinical need exists for pharmacological agents which can diagnose, treat or prevent such disorders by inducing relaxation of the affected gastrointestinal smooth muscle without adverse effects. There is also a clinical need for pharmacological agents to induce the relaxation of gastrointestinal smooth muscle to facilitate diagnostic and therapeutic gastrointestinal medical procedures.

SUMMARY OF THE INVENTION

This invention is based on the discovery that ethyl nitrite exerts a potent and reversible relaxant effect on gastrointestinal smooth muscle. This concept led to the discovery that formulations comprising ethyl nitrite can be used as a diagnostic or therapeutic modality in disorders which involve gastrointestinal smooth muscle relaxation.

The present invention provides a composition comprising a gas and a gastrointestinal smooth muscle relaxing agent comprising ethyl nitrite in a therapeutically effective amount ranging from 0.1 to 1000 ppm.

The gas can be nitrogen or oxygen. Preferably, the gas is nitrogen. The therapeutically effective amount can range from 0.1 to 100 ppm. The therapeutically effective amount can also range from 0.1 to 10 ppm. Preferably, the gas comprises minimal impurities. More preferably, the gas comprises less than 5 ppm $NO_2$, less than 25 ppm NO and/or less than 48 ppmv ethanol.

The present invention also provides methods of relaxing gastrointestinal smooth muscle in a subject in need thereof comprising contacting said smooth muscle with a composition comprising a gas and a gastrointestinal smooth muscle relaxing agent comprising ethyl nitrite in a therapeutically effective amount.

The present invention also provides methods of alleviating contraction or spasm of gastrointestinal smooth muscle associated with a medical procedure in a subject comprising contacting said smooth muscle with a composition comprising a gas and a gastrointestinal smooth muscle relaxing agent comprising ethyl nitrite in a therapeutically effective amount.

The medical procedure can be an endoscopic procedure. Preferably, the endoscopic procedure is enteroscopy, esophagogastroduodenoscopy (EGD), endoscopic retrograde cholangiopancreatography (ERCP), colonoscopy or sigmoidoscopy. The compositions of the invention can relax any gastrointestinal smooth muscle. Preferably, the gastrointestinal smooth muscle is the sphincter of Oddi.

The present invention also provides methods of diagnosing, treating or preventing a gastrointestinal disorder associated with smooth muscle constriction in a subject in need thereof comprising administering a therapeutically effective amount of a composition comprising a gas and a gastrointestinal smooth muscle relaxing agent comprising ethyl nitrite to said subject thereby relaxing said gastrointestinal smooth muscle and diagnosing, treating or preventing said gastrointestinal disorder.

Gastrointestinal disorders to be diagnosed or treated include but are not limited to: gastrointestinal spasm, achalasia, diarrhea, dumping syndrome, irritable bowel syndrome, constipation, dyspepsia, gastroparesis, and gastroesophageal reflux disease. The compounds of the invention can be administered by any means known in the art. Preferably, the compounds are administrated topically. Preferably, the agent does not form $NO_2$ or $NO_x$ in the presence of oxygen or reactive oxygen species at body temperature.

The present invention also provides methods for producing ethyl nitrite comprising the steps of (a) mixing sodium nitrite and ethanol to form a first solution; and (b) adding a second solution comprising sulfuric acid and ethanol to the first solution, wherein the rate of addition of the second solution provides a reaction temperature which enhances conversion. Preferably, the ethyl nitrite is produced in at least 92% yield. Preferably, the reaction temperature is between 0-30° C. The first solution and/or second solution can be homogenous. The mixing of the first solution and/or the addition of the second solution can further include a nitrogen purge. The rate of addition can be drop wise. Preferably, the rate of addition is such that the reaction temperature remains below 30° C. The ethyl nitrite is collected into an ice chilled receiving flask and can be stored under an inert atmosphere.

The present invention also provides methods for producing ethyl nitrite in nitrogen comprising the steps of (a) introducing ethyl nitrite which comprises less than 3% (by weight) ethanol to an evacuated cylinder; (b) adding nitrogen gas to the cylinder; and, (c) homogenizing the ethyl nitrite and nitrogen gas in the cylinder, such that the ethyl nitrite in nitrogen comprises less than 5 ppm nitrogen dioxide. The ethyl nitrite in nitrogen further comprises less than 25 ppm nitric oxide. Preferably, the ethyl nitrite in nitrogen is at about 1000 ppm at a final cylinder pressure of approximately 900 psi. Higher and lower final ethyl nitrite concentrations are achievable by adjusting the final cylinder pressures appropriately. The ethyl nitrite in nitrogen can be stable for at least two years. Preferably, the ethyl nitrite in step (a) is introduced at about 5.625 G. Preferably, the cylinder is evacuated to at least 10 microns prior to addition of ethyl nitrite. Preferably, the ethyl nitrite in step (a) is introduced to the cylinder by gas-tight syringe. Preferably, the nitrogen gas in step (b) is added at about 2.1 kG. Preferably, the nitrogen gas in step (b) is added by means of a high purity stainless steel manifold. Preferably, the homogenization in step (c) occurs by rolling the cylinder on a four position cylinder roller for at least 30 minutes.

DETAILED DESCRIPTION OF THE INVENTION

The present invention provides a composition comprising a gas and a gastrointestinal smooth muscle relaxing agent comprising ethyl nitrite in a therapeutically effective amount. Ethyl nitrite has the formula: $CH_3CH_2ONO$ and is also referred to as O-nitrosoethanol. The terms "ethyl nitrite", "O-nitrosoethanol" and "ENO" are used interchangeably herein.

When the ethyl nitrite is administered as part of a gas, it must be formulated so as to produce a homogenous gas blend for administration. The ethyl nitrite is not expected to harm the gastrointestinal tract or condense in the gastrointestinal tract. Ethyl nitrite is available commercially, e.g., diluted in ethanol; however, this mixture is not suitable for preparation of homogenous gas blends as described herein. The ethyl nitrite can be admixed with an inert gas to provide the gas for administration, e.g., by conventional gas blending methods or more preferably by the methods described herein. The inert gas can be nitrogen or oxygen, or a mixture thereof. Preferably, the composition of the present invention comprises ethyl nitrite in nitrogen.

Preferably, the ethyl nitrite is produced as a homogenous gas blend in nitrogen as described herein. Thus, the present invention also provides methods for producing ethyl nitrite comprising the steps of (a) mixing sodium nitrite and ethanol to form a first solution; and (b) adding a second solution comprising sulfuric acid and ethanol to the first solution, wherein the rate of addition of the second solution provides a reaction temperature which enhances conversion. Preferably, the ethyl nitrite is produced in at least 92% yield. Preferably, the reaction temperature is between 0-30° C. The first solution and/or second solution can be homogenous. As used herein, the term "homogenous" means that all of the solids are dissolved. The mixing of the first solution and/or the addition of the second solution can further include a nitrogen purge. The rate of addition can be drop wise. Preferably, the addition is at a rate such that the reaction temperature remains below 30° C. The ethyl nitrite is collected into an ice chilled receiving flask and can be stored under an inert atmosphere.

The present invention also provides methods for producing ethyl nitrite in nitrogen comprising the steps of (a) introducing ethyl nitrite which comprises less than 3% (by weight) ethanol to an evacuated cylinder; (b) adding nitrogen gas to the cylinder; and, (c) homogenizing the ethyl nitrite and nitrogen gas in the cylinder, such that the ethyl nitrite in nitrogen comprises less than 5 ppm nitrogen dioxide. The ethyl nitrite in nitrogen further comprises less than 25 ppm nitric oxide. Preferably, the ethyl nitrite in nitrogen is at about 1000 ppm. The ethyl nitrite in nitrogen can be stable for at least two years. Preferably, the cylinder is evacuated to at least 10 microns prior to addition of ethyl nitrite. Preferably, the ethyl nitrite in step (a) is introduced at about 5.625 G. Preferably, the ethyl nitrite in step (a) is introduced to the cylinder by gas-tight syringe. Preferably, the nitrogen gas in step (b) is added at about 2.1 kG. Preferably, the nitrogen gas in step (b) is added by means of a high purity stainless steel manifold. Preferably, the homogenization in step (c) occurs by rolling the cylinder on a four position cylinder roller for at least 30 minutes.

Where the ethyl nitrite is administered as part of a gas, it is administered in a therapeutically effective amount ranging from 0.1 to 1000 ppm. The therapeutically effective amount can range from 0.1 to 100 ppm. The therapeutically effective amount can also range from 0.1 to 10 ppm. As an example, if the therapeutically effective amount is from 0.1 to 10 ppm, the therapeutically effective amount can be any specific amount within the range of 0.1 to 10 ppm (e.g., 0.1, 0.2 . . . 1, 2, 3, 4, 5, 6, 7, 8, 9, 10 ppm, or any fraction thereof). The therapeutically effective amount can also be any range within 0.1 to 10 ppm (e.g., 0.1 to 2, 0.1 to 3 . . . 0.1 to 10, 0.2 to 3, 0.2 to 4 . . . 0.2 to 10, etc. or any fraction thereof). Preferably, the gas comprises minimal impurities. More preferably, the gas comprises less than 5 ppm $NO_2$, less than 25 ppm NO and/or less than 48 ppmv ethanol.

These compounds may be used to diagnose, treat or prevent those pathophysiologic conditions which result from, or involve, constriction of smooth muscle, or those which necessitate therapeutic intervention to achieve smooth muscle relaxation.

The invention also relates to the administration of a therapeutically effective amount of compounds comprising ethyl nitrite to a subject to relax gastrointestinal smooth muscle. The term "gastrointestinal smooth muscle" refers to smooth muscle which is contained within areas of the gastrointestinal tract. Such areas include the entire luminal gastrointestinal tract and its appendages, including the biliary tree and pancreatic duct. Compounds comprising ethyl nitrite can also be used for the treatment or prevention of gastrointestinal disorders. Disorders of the gastrointestinal tract include, but are not limited to, gastrointestinal spasm, achalasia (spasm of the lower esophageal sphincter), diarrhea, dumping syndrome, irritable bowel syndrome, constipation, dyspepsia, gastroparesis, and gastroesophageal reflux disease, Additionally, the invention relates to the administration of compounds comprising ethyl nitrite to alleviate contraction or spasm of gastrointestinal smooth muscle, and thus facilitate successful completion of diagnostic and therapeutic endoscopic procedures. Contraction or spasm of gastrointestinal smooth muscle imposes a technical obstacle which must frequently be overcome in order to enable the clinician to successfully, perform endoscopic procedures.

The term "endoscopic procedures" refers to those diagnostic or therapeutic procedures which utilize an instrument which is introduced into the gastrointestinal tract to provide direct visualization of the gastrointestinal tract, for examination and therapeutic purposes. Such purposes include direct visualization, biopsy, access to the common bile duct, fluid aspiration and removal of foreign bodies, polyps, and other lesions. An example of a particular endoscopic procedure is esophagogastroduodenoscopy (EGD), which is utilized for examination of the esophageal lumen, stomach and duodenum. Another example, endoscopic retrograde cholangiopancreatography (ERCP), enables visualization of the pancreatic duct, common bile duct and the entire biliary tract, including the gall bladder. Further examples of endoscopic procedures are enteroscopy, colonoscopy and sigmoidoscopy.

Current methods for alleviating gastrointestinal muscle spasm include the administration of anticholinergics and glucagon, as well as sublingual administration of nitroglycerin. However, these methods produce generalized, systemic effects which persist for a much longer duration than the procedure itself. In addition, nitroglycerin is significantly less effective as a smooth muscle relaxant than ethyl nitrite, produces systemic side effects, the most significant of which is hypotension, and is therefore, not used clinically. Clearly, a need exists for a topical smooth muscle relaxant which could be directly instilled into the various regions of the gastrointestinal tract to facilitate both diagnostic and therapeutic endoscopic procedures.

Limited pharmacological agents exist which can be applied directly by endoscopic means to exert a direct, immediate, localized, and completely reversible relaxant effect on gastrointestinal smooth muscle. Ethyl nitrite can be efficacious in facilitating cannulation of the sphincter of Oddi. Topical administration of ethyl nitrite can modify duodenal motility and inhibit the contractile activity of the sphincter of Oddi and thus, permit successful endoscopic cannulation of the sphincter. In addition, administration of ethyl nitrite can eliminate colon motility to facilitate successful removal of colon polyps. Notably, the relaxant effects are temporary (lasting only for the duration of the procedure), completely reversible and produce no change in systemic blood pressure, heart rate or oxygen saturation. Topical or local administration of ethyl nitrite, during endoscopy, does not produce systemic side effects and allows for the use of the lowest effective concentration of the drug.

Administration of ethyl nitrite reduces the time and increases the ease of endoscopic procedures, and obviates the need for sphincterotomy, a procedure which substantially increases the morbidity and mortality of ERCP. In addition, administration of ethyl nitrite aids in the cannulation and manipulation of the pancreatic duct and biliary tract during therapeutic procedures such as gall bladder cannulation, bile duct stone removal and stent placement, and decreases the incidence of post-ERCP complications, such as pancreatitis, cholangitis and spasm. In addition to the uses discussed above, ethyl nitrite can also be administered to treat or prevent any other technical problems associated with endoscopy which are known to those in the medical art.

It is preferred that when the compositions of the invention are administered to a subject for therapeutic or diagnostic purposes, the gastrointestinal smooth muscle relaxing agent comprising ethyl nitrite does not form $NO_2$ or $NO_x$ in the presence of oxygen or reactive oxygen species at body temperature or exert systemic blood pressure compromising effect.

Many gastrointestinal illnesses are associated with inflammation, thus advantages of the methods described herein include: administration of ethyl nitrite reduces the toxicity caused by $NO_2/NO_x$ formation as compared to when NO is administered (i.e., ethyl nitrite does not react with $O_2$ to produce pro-inflammatory (toxic) $NO_x$); the option of administering the compound comprising ethyl nitrite together with oxygen, without $NO_2/NO_x$ production; some patients respond to administration of ethyl nitrite who do not respond to administration of NO. Additionally, since the gastrointestinal tract of a subject is filled with gas during endoscopic procedures, providing a smooth muscle relaxant in gaseous form is a desirable and unique means of delivery. Additional advantages of administering ethyl nitrite as a gas include: biocompatibility, ease of clearance, local delivery, delivery across large surface areas, and readily adjustable dosing.

As used herein the term "$NO_x$" means NO, $N_2O_3$, $N_2O_4$, $OONO^-$, $OONO^-$ and any products of their interaction or their reaction with NO or $NO_2$. As used herein the term "reactive oxygen species" is singlet oxygen, superoxide, hydrogen peroxide or hydroxyl radical.

According to the present invention, a "therapeutically effective amount" of a pharmaceutical composition is an amount which is sufficient to achieve the desired pharmacological effect. Preferably, the desired pharmacological effect is the relaxation of gastrointestinal smooth muscle. Generally, the dosage required to provide an effective mount of the composition, and which can be adjusted by one of ordinary skill in the art, will vary, depending upon the particular pathophysiology and the age, health, physical condition, sex, weight and extent of disease, of the recipient. Additionally, the dosage may be determined by the frequency and duration of treatment and the nature and scope of the desired effect.

Administration can be carried out for as long as needed. The dosage will vary from patient to patient. Upon administration, results are noted with variation in dosage and then the dosage is preferably used which results in achievement of best results. The most effective dosage can be lower than some of the dosages tried; thus, if after increases in dosage are tried, an increased dosage provides less improvement, then return to the more effective lower dose is indicated.

The compositions utilized in this invention can be administered by any means known in the art, for example, topical, inhalation, intranasal or local means. Preferably, the compositions of the present invention are administered or utilized topically or locally. Preferably, the compositions are delivered to the gastrointestinal tract as part of a gas. The compositions may be administered by medical instrumentation including, but not limited to, endoscopic means.

Preferably, the method comprises the topical administration of the compositions of the invention. The terms "topical", "topically", "topical application", "applied topically", "topical administration" and "administered topically", are used interchangeably here in their conventional sense as referring to a spot, which can be in or on any part of the body, including but not limited to smooth muscle, the epidermis, any other dermis, or any other body tissue. Topical administration or application means the direct contact of the composition with tissue, such as smooth muscle, skin or membrane.

The compositions of the present invention comprising ethyl nitrite can further comprise a pharmaceutically acceptable carrier, to achieve the physiological effects described herein. The compounds of this invention can be employed in combination with conventional excipients; i.e., pharmaceutically acceptable organic or inorganic carrier substance suitable for the proposed method of application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

It will be appreciated that the actually preferred amounts of ethyl nitrite used will vary according to the specific compound being utilized, the particular compositions formulated, the mode of application and the particular site of administration. Optimal administration rates for a given protocol of administration can be readily ascertained by those skilled in the art, using conventional dosage determination tests conducted with regard to the foregoing guidelines. Ampules are convenient unit dosages.

Without further elaboration, it is believed that one skilled in the art can, using the preceding description, utilize the present invention to its fullest extent. The following examples are, therefore, to be construed as merely illustrative, and not limitative of the remainder of the disclosure in any way whatsoever.

The entire text of all publications cited above and below is hereby incorporated herein by reference.

EXAMPLES

Example 1

Ethyl nitrite is readily delivered to a subject in gaseous form. As known to those ordinarily skilled in the art, ethyl nitrite is produced by bubbling nitrogen or oxygen through a Fisher-Milligan ("FM") gas diffuser containing ethyl nitrite diluted in ethanol (e.g., from 0.00125 to 0.5% ethyl nitrate in ethanol (v/v), preferably from 0.0025 to 0.125% ethyl nitrite in ethanol (v/v)), e.g., at a flow rate of 0.5 liters/min to 1.5 liters/min, to produce nitrogen or oxygen containing ethyl nitrite. The actual composition of the gas resulting from this type of exposure has been assessed by Fourier Transform Infrared Spectroscopy (FTIR). As is apparent from the following study and resulting data, however, the EtOH content provided to patients by methods of the prior art was significantly higher (e.g., 30× more ethanol was delivered than ENO) than in the present invention, wherein the constant concentration of EtOH is less than 48 ppmv in the ENO/EtOH composition.

Materials/Methods 200 ml of solution of ethyl nitrite in ethanol (final concentrations as given below) was loaded into the FM gas diffuser and 1 LPM flow of air was delivered for 1 hour. Effluent gas from the FM was combined with an additional 9 LPM of air post-FM and the resulting gas was analyzed by FTIR for concentration of ENO and ethanol. FTIR data was collected at 0.5 wave number resolution with 128 scans over the range of 650-4000 wave numbers. FTIR gas cell length is 6.5 meters, cell pressure was ~5 psig (controlled), and temperature was 150° F. (controlled). Sample flow was controlled at 3 LPM through the FTIR gas cell. A water vapor spectrum was taken and subtracted from the data prior to quantitation. The ENO quantitation was performed using the region of 1722-1572 wave numbers. Data was collected approximately every ten minutes and, in the low and mid concentration ranges, data was taken 2 minutes into the run. FTIR analyses took 2.5 minutes to run and represent an average value over that time.

For ENO measurement, a calibration curve was prepared using a 250 ppm ENO/N2 standard and a 10 point capillary gas divider. For ethanol, a single ethanol standard prepared at 2000 ppm in nitrogen was used to estimate the quantity of ethanol in the delivered gas stream.

ENO/EtOH Concentrations Used in FM Experiments:

High Conc—1.4 mL of ENO/ETOH solutions from Aldrich (17.8% conc) diluted to 200 mL solution (i.e., 0.125%)

Mid Conc—0.28 mL of ENO/ETOH solutions from Aldrich (17.8% conc) diluted to 200 mL solution (i.e., 0.025%)

Low Conc—0.028 mL of ENO/ETOH solutions from Aldrich (17.8% conc) diluted to 200 mL solution (i.e., 0.0025%)

Results of ENO Analyses

The results of the ENO analyses are provided in Table 1 below. As is apparent from the results, the ENO content provided to patients by methods of the prior art was likely significantly more variable over time than the content provided by the methods of the current invention:

TABLE 1

| ENO in EtOH concentration (% volume) | Time after initiation of volatilization (min) | ENO (ppm) |
|---|---|---|
| 0.125% | 10 | 281.4 |
|  | 20 | 141.5 |
|  | 30 | 66.9 |
|  | 40 | 34.9 |
|  | 50 | 15.8 |
|  | 60 | 5.1 |
| 0.025% | 2 | 104.2 |
|  | 10 | 59.8 |
|  | 20 | 29.1 |
|  | 30 | 15.2 |
|  | 40 | 7.5 |
|  | 50 | 3.7 |
|  | 60 | 1.4 |
| 0.0025% | 2 | 16.2 |
|  | 17 | 6.8 |
|  | 20 | 5.2 |
|  | 30 | 2.4 |
|  | 40 | 1.0 |
|  | 50 | 0.1 |
|  | 60 | −0.2 |

Results of Ethanol Analyses

The ethanol amounts varied with time over the course of the vaporization but less than 10% over the hour. Variance was probably due cooling of the solution as the gas vaporized. The ethanol was quantified over the region of 3762-3551 wave numbers. The results were scaled to the standard as a simple linear relationship. The quantitation results represent a lower limit of the actual values. As can be seen, the ethanol concentrations delivered in the prior art (represented in Table 2) were significantly higher than the concentrations delivered by the methods in the current invention (e.g., less than 48 ppmv).

TABLE 2

| ENO in EtOH concentration (% volume) | EtOH concentration measured (ppm) |
|---|---|
| 0.125% | ~6000-6700 ppm |
| 0.025% | ~5900-6600 ppm |
| 0.0025% | ~5800-6100 ppm |

Example 2

Liquid ethyl nitrite is synthesized in one step from ethanol by nitrosylation under acidic conditions as described (Org. Syn. Coll. Vol. 2, A H Blatt ed, 1943, p 204-205). The product distills from the reaction mixture and is isolated by collection of the condensate. The isolated product can be used with or without further purification for blending of the pharmaceutical composition.

The synthesis of ethyl nitrite is shown below and the appropriate reagents and solvents used for the reaction are shown in Table 3. Preferably, the yield of the reaction is greater than 92%.

TABLE 3

$$CH_3CH_2OH + NaNO_2 \xrightarrow[N_2, 0-15°C]{H_2SO_4} CH_3CH_2ONO$$

| | Typical Quantity | Typical Quantity (Grams) | Typical Quantity (Moles) |
|---|---|---|---|
| Ethanol | 180 ml | 142 g | 3.08 |
| Sodium nitrite | 210 g | 210 g | 2.47 |
| Sulfuric acid | 90 ml | 165.6 g | 1.69 |
| DI Water | 1360 ml | 1360 g | 75.5 |
| Ethyl Nitrite | 170 g | 170 g | 2.27 |

The following description of the synthesis represents typical charge quantities and yields. Reactions of larger or smaller scale may be performed with adjustment of reagent charges.

1. Solution 1: Approximately 90 mL of ethanol, 725 mL of water, and 210 grams of sodium nitrite are combined in an appropriate vessel with stirring. The vessel is purged with nitrogen and the material stirred until all solids dissolve resulting in a pale yellow solution.
2. Solution 2: Approximately 90 mL of sulfuric acid, 90 mL of ethanol, and 632 mL of water are combined and mixed to assure homogeneity.
3. Solution 2 is added to Solution 1 under nitrogen in a drop wise manner at a rate such that the reaction temperature remains below 30° C. while the temperature of the condenser is maintained between 0-10° C.
4. The ethyl nitrite product distills into the ice water chilled receiving flask over the course of the reaction and visibly stops collecting near the end of the addition of Solution 2.
5. The product is transferred to an aluminum or glass bottle under an inert atmosphere and stored under refrigeration.

The specifications preferred for ethyl nitrite liquid prepared from the foregoing procedure are shown in Table 4.

TABLE 4

| TEST | ACCEPTANCE CRITERIA |
|---|---|
| Assay (by GC): | >97.0% |
| Ethanol (by GC): | <3.0% (weight) |

TABLE 4-continued

| TEST | ACCEPTANCE CRITERIA |
|---|---|
| MeOH (by GC): | <3000 ppm |
| Acetone (by GC): | <5000 ppm |
| Total impurities (by GC): | <3.0% |
| Unidentified impurities (by FTIR): | NMT 30.0 ppm |
| Nitric oxide (FTIR) | NMT 25.0 ppm |
| Nitrogen dioxide (FTIR) | NMT 3.0 ppm |
| Water (FTIR) | Absence of water confirmed |
| Sulfuric acid (FTIR) | Absence of sulfuric acid confirmed |
| Appearance: | Clear liquid, colorless to yellow |
| Identification (FTIR) | Spectrum consistent with reference standard spectrum |
| Identification (GC) | GC retention time is consistent with reference spectrum |

The ethyl nitrite synthesis process was optimized by conducting a series of experiments in which parameters of reaction temperature and rate of addition of solution 2 were varied.

Ethyl nitrite in nitrogen can be prepared by blending ethyl nitrite liquid in nitrogen to form a homogeneous gas blend at a preferred concentration of 1000 ppm and preferred pressure of approximately 900 psi. The blending is performed gravimetrically in accordance with standard compressed gas manufacturing procedures familiar to those skilled in the art. Manufacturing information is provided below for the preferred concentration of ethyl nitrite in nitrogen, 1000 ppm. Other final blend concentrations can be prepared as required according to these instructions with the appropriate modifications to ethyl nitrite and nitrogen gas charge quantities. The material specifications are shown in Table 5.

TABLE 5

| Component | Description | Specification |
|---|---|---|
| Nitrogen | NF grade | NF |
| Compressed gas cylinder | T6061 aluminum Luxfer USA model 152 | 3AL2015 |
| Compressed gas cylinder valve | Stainless Steel packless diaphragm valve Ceodeux model 098377000000 | CGA-350 Stainless Steel valve with packless diaphragm |

Figure 1:
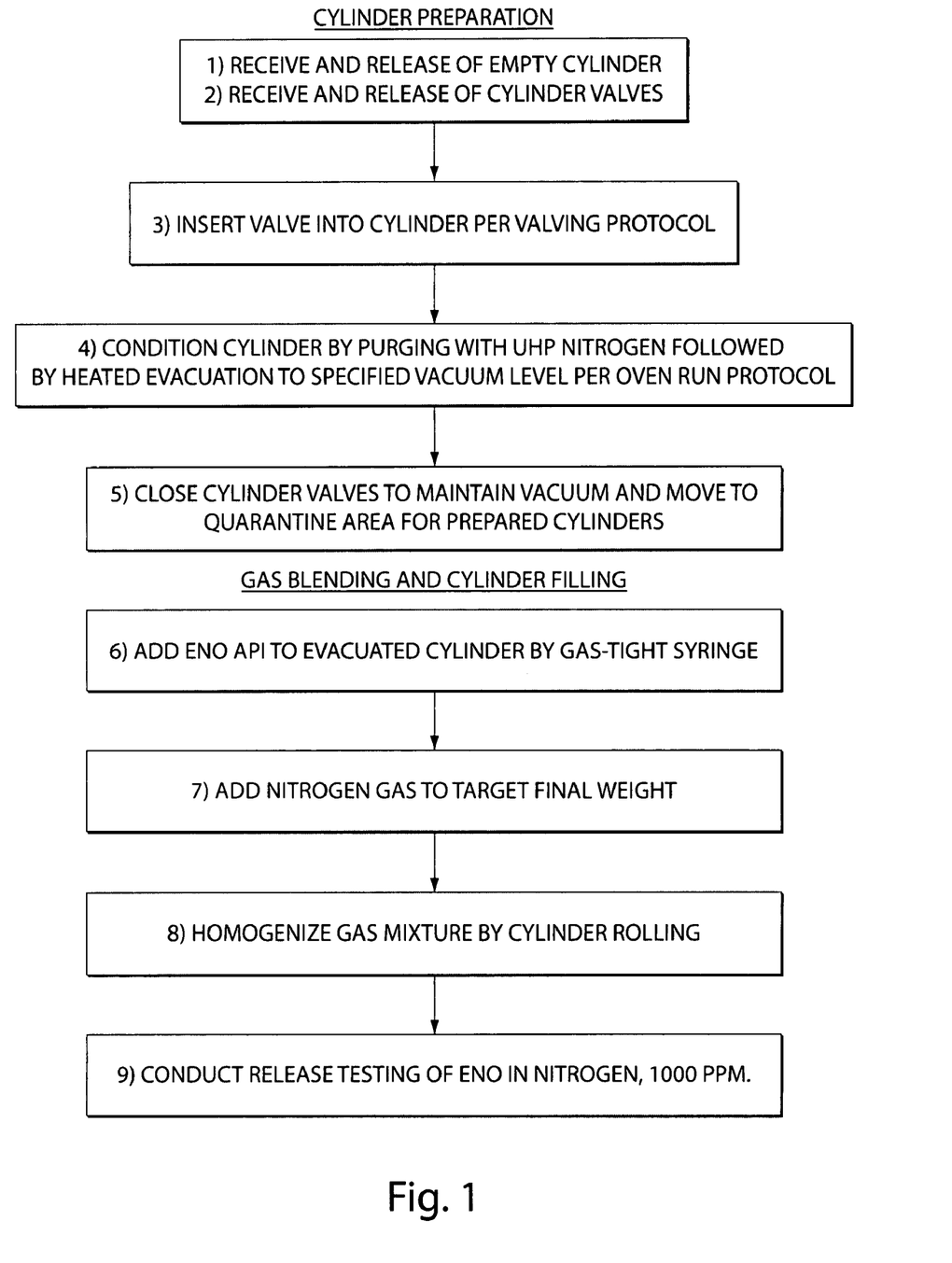
FIG. 1 is a schematic flow chart illustrating cylinder preparation, gas blending and cylinder filling.

A Flow Chart of the Manufacturing Process is shown in FIG. 1. The following is a stepwise description of a preferred manufacturing process:

1. Empty aluminum cylinders are placed in a cylinder oven and connected to a stainless steel manifold with purge and evacuation capabilities. The manifold is opened to a vacuum pump and the integrity of the system is tested (vacuum must be better than 10 microns). The oven heater/blower is activated and set to 150° F. The vacuum is shut off and the cylinder valves are opened to the manifold. High-pressure nitrogen is allowed to flow into the cylinders to a final pressure of ~100 psig and then vented to atmosphere. This procedure is repeated a total of three times. After the final purge cycle, the manifold is isolated from the purge gas supply and vent and placed under vacuum. The cylinders are allowed to evacuate under heated conditions until the vacuum achieved is better than 10 microns (usually ~2 hours time). The cylinder valves are closed and the cylinders are removed from the oven under vacuum and placed in the quarantine area for prepared cylinders.
2. Ethyl nitrite liquid as prepared above, ~5.625 G, is withdrawn into a gas-tight syringe and is added to an evacuated cylinder.

3. Nitrogen, approximately 2.1 kG, is added with the resulting pressure typically being 850-1000 psi.
4. The gaseous mixture is homogenized by rolling for no less than ½ hour.
5. The cylinders are then tested and stored at ambient warehouse conditions.

Ethyl nitrite in nitrogen, 1000 ppm, is stable for at least two years after manufacture when stored under standard compressed gas cylinder conditions (typical warehouse conditions). The specifications preferred for ethyl nitrite in nitrogen, 1000 ppm, prepared from the foregoing procedure are shown in Table 6.

TABLE 6

| TEST | ACCEPTANCE CRITERIA |
|---|---|
| Assay (GC): | 900-1100 ppmv |
| Ethanol (GC) | <48 ppmv |
| Nitric oxide (FTIR) | <25 ppm |
| Nitrogen dioxide (FTIR) | <3 ppm |
| Water (FTIR) | Absence of water confirmed |
| Sulfuric acid (FTIR) | Absence of sulfuric acid confirmed |
| Appearance | Colorless gas |
| Identification (Infrared spectroscopy) | Spectrum consistent with reference standard spectrum |
| Identification (GC) | GC retention time is consistent with reference spectrum |

Example 3

The present experiment is conducted to relax the sphincter of Oddi by administering a composition comprising ethyl nitrite to facilitate ERCP. Upwards of 500,000 ERCPs are performed each year in the United States. Post-procedural complications include pancreatitis, infection, bleeding, and tissue perforation, the rates of which have been estimated to be as high as 20%. A therapeutic intervention that can facilitate ERCP and by extension reduce the associated morbidity is of significant clinical importance.

ERCP is a procedure conducted by gastroenterologists to diagnose and/or correct problems in the liver, gallbladder, bile ducts, and pancreas. It involves the insertion of an endoscope through the esophagus, stomach, and duodenum until it reaches the point where the ducts of the biliary tree and pancreas open into the duodenum. The juncture is the sphincter of Oddi (SO). Subsequent assessment of biliary and pancreatic function requires insertion of a catheter through the sphincter. It is this step that is associated with significant morbidity because of the mechanical trauma induced by pushing the catheter against the contracted smooth muscle—in essence one is attempting to push an object in the opposite direction through a one way valve. Direct application of an agent such as ethyl nitrite that can inhibit duodenal and SO muscle activity greatly reduces the incidence of post-ERCP complications; note that systemic administration is not a viable option because any drug that sufficiently inhibits the SO smooth muscles would also produce significant hypotension.

The present study utilizes young adult swine since their SO functions similarly to humans; the animals are of sufficient size to accept a human endoscope and provide enough blood for post-procedural assessments; and the swine have been used previously by other research groups to study ERCP and to mimic SO and biliary/pancreatic dysfunction.

For the present experiments, 100 ppm ethyl nitrite in nitrogen is utilized. Dosing of individual animals is in a range of 0.1 to 100 ppm. Dosages are delivered via endoscope.

Preliminary non-survival experiments are conducted to narrow down the effective ethyl nitrite dose and identify any unexpected experimental complications. The main study is conducted on pigs under a combination of midazolam and propofol anesthesia.

In the study, a group of 3 animals are heavily sedated. Following sedation, the animals are intubated and venous and arterial catheters are installed. tStat probe (Spectros; metHb detection) and other monitoring devices are prepared. Blood samples (approximately 1 ml) to monitor blood gas status are also obtained.

Figure 2:
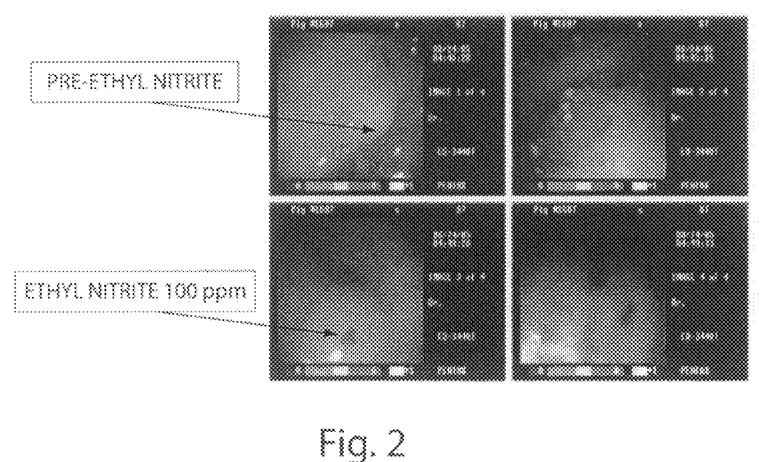
FIG. 2 is a series of photographs showing the diameter of the sphincter of Oddi prior to treatment with ethyl nitrite and following treatment with 100 ppm of ethyl nitrite in nitrogen.
Figure 3:
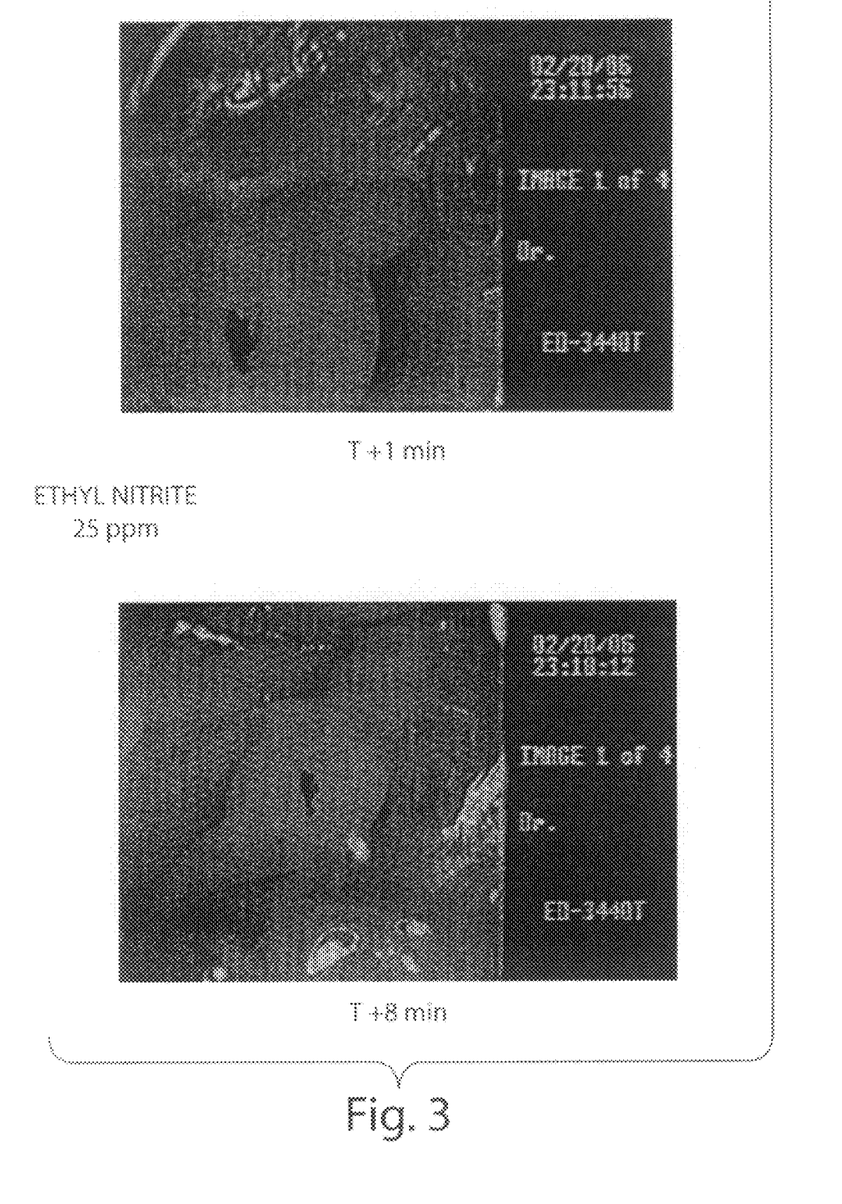
FIG. 3 is a series of photographs showing relaxation in the diameter of the sphincter of Oddi produced by 25 ppm ethyl nitrite in nitrogen at one minute (top panel) and eight minutes (bottom panel) following treatment.
Figure 4:
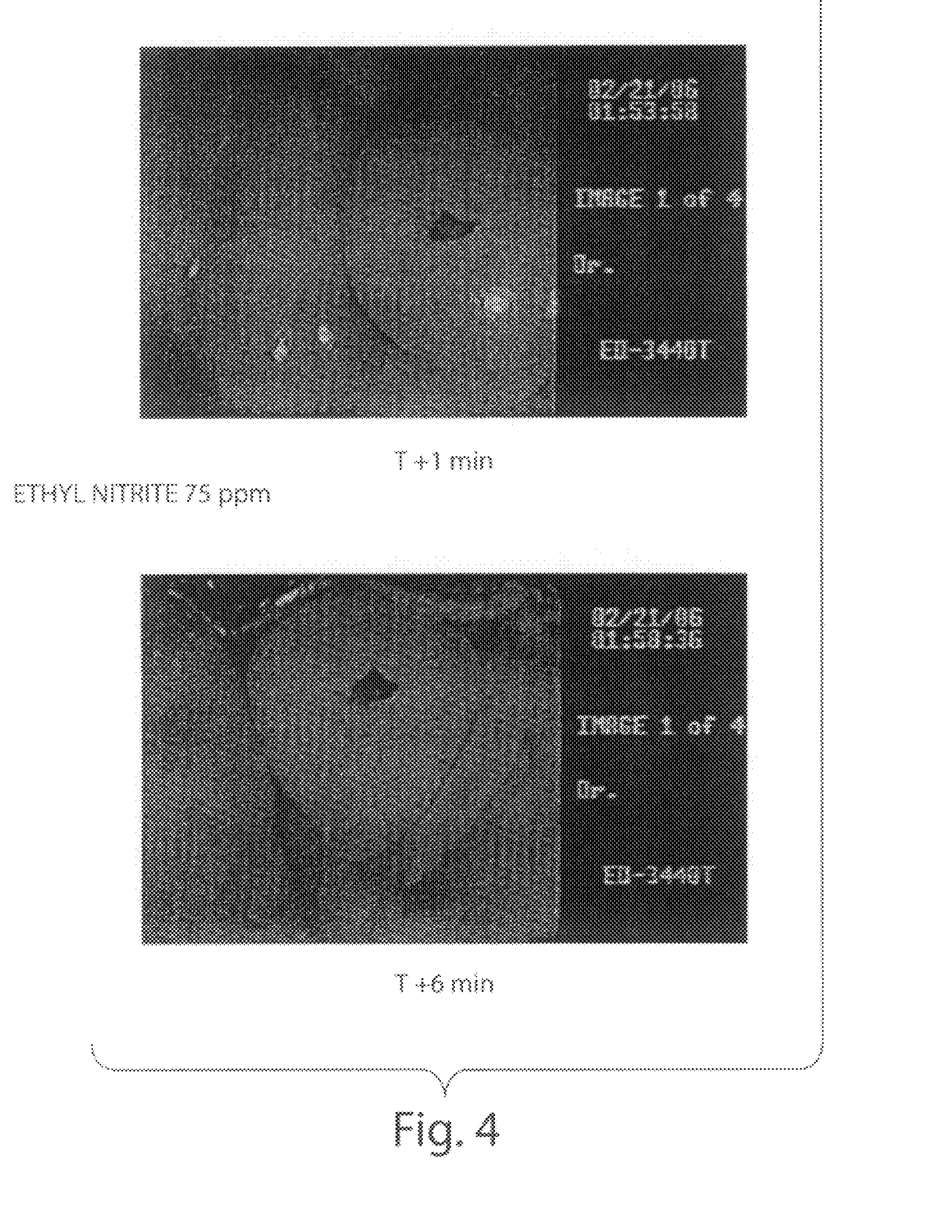
FIG. 4 is a series of photographs showing relaxation in the diameter of the sphincter of Oddi produced by 75 ppm ethyl nitrite in nitrogen at one minute (top panel) and six minutes (bottom panel) following treatment.
Figure 5:
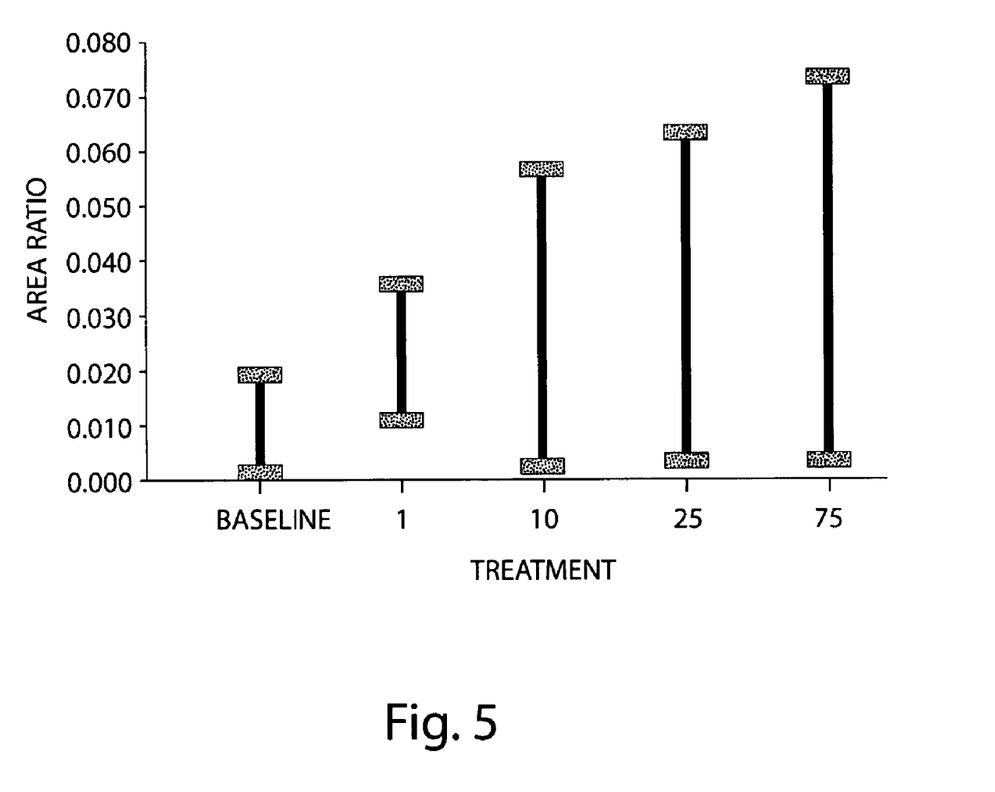
FIG. 5 is a graph showing changes in sphincter/papilla area ratio relative to ethyl nitrite concentration.

In the procedure, an endoscope is inserted in the duodenum and the duodenum is inflated according to standard clinical practice. The sphincter is identified. Following the recordation of baseline recordings, an approximate 20-30 second stream (flow rate of 5 L/min) of ethyl nitrite in nitrogen is directed on to the papilla and any changes in sphincter diameter are recorded. The process is repeated with serial increases in ethyl nitrite in nitrogen; 0, 1, 10, 25, 50, 75, and 100 ppm. The interval between applications is 30 minutes. Throughout the experiment, blood gases are determined at regular intervals. Each procedure was videotaped and images were captured offline. The results in FIG. 2 show a distinct and prolonged relaxation produced by 100 ppm ethyl nitrite in nitrogen. FIG. 3 shows relaxation produced by 25 ppm ethyl nitrite in nitrogen at one minute and eight minutes following treatment. FIG. 4 shows relaxation produced by 75 ppm ethyl nitrite in nitrogen at one minute and six minutes following treatment. Area calculations were carried out using Image J software. Sphincter measurements were normalized to the papilla area which accounted for variability in image depth, view area, etc. The changes in sphincter/papilla area ration relative to ethyl nitrite concentration are shown in FIG. 5. The overall results show a quick and direct effect on the target tissue with minimal systemic effects and no measurable increase in methemoglobin was detected.

In the procedure, an endoscope is inserted in the duodenum and the duodenum is inflated according to standard clinical practice. Following the recordation of baseline and stimulated pressure recordings, an approximate 20 second stream of nitrogen alone or admixed with ethyl nitrite is directed on to the papilla and any changes in sphincter activity are recorded. Following relaxation, sphincter cannulation can proceed. The post-cannulation response is measured in decreases in gastrointestinal motility, reduced procedure time and increase ease of cannulation procedure and comparison between control and ethyl nitrite-exposed animals is carried out.

What is claimed:
1. A method of relaxing gastrointestinal smooth muscle in a subject in need thereof comprising topically contacting said smooth muscle with a gaseous composition comprising a homogenous blend of nitrogen and ethyl nitrite in a therapeutically effective amount, wherein said gaseous composition comprises less than 48 ppmv ethanol, wherein the gaseous composition is delivered to the gastrointestinal tract of the subject.
2. The method of claim 1, wherein the therapeutically effective amount ranges from 0.1 to 1000 ppm.
3. The method of claim 1, wherein the therapeutically effective amount ranges from 0.1 to 100 ppm.
4. The method of claim 1, wherein the therapeutically effective amount ranges from 0.1 to 10 ppm.
5. The method of claim 1, wherein said gas comprises less than 5 ppm NO2.
6. The method of claim 1, wherein said gas comprises less than 25 ppm NO.

7. A method of alleviating contraction or spasm of gastrointestinal smooth muscle associated with a medical procedure in a subject comprising topically contacting said smooth muscle with a gaseous composition comprising a homogenous blend of nitrogen and ethyl nitrite in a therapeutically effective amount, wherein said gas comprises less than 48 ppmv ethanol, wherein the gaseous composition is delivered to the gastrointestinal tract of the subject.

8. The method of claim 7, wherein the therapeutically effective amount ranges from 0.1 to 1000 ppm.

9. The method of claim 7, wherein the therapeutically effective amount ranges from 0.1 to 100 ppm.

10. The method of claim 7, wherein the therapeutically effective amount ranges from 0.1 to 10 ppm.

11. The method of claim 7, wherein said gas comprises less than 5 ppm NO2.

12. The method of claim 7, wherein said gas comprises less than 25 ppm NO.

13. The method of claim 7, wherein the medical procedure is an endoscopic procedure.

14. A method of treating a gastrointestinal disorder associated with smooth muscle constriction in a subject in need thereof comprising topically administering a therapeutically effective amount of a gaseous composition comprising a homogenous blend of nitrogen and ethyl nitrite to said subject thereby relaxing said gastrointestinal smooth muscle and treating said gastrointestinal disorder, wherein said gas comprises less than 48 ppmv ethanol, wherein the gaseous composition is delivered to the gastrointestinal tract of the subject.

15. The method of claim 14, wherein the therapeutically effective amount ranges from 0.1 to 1000 ppm.

16. The method of claim 14, wherein the therapeutically effective amount ranges from 0.1 to 100 ppm.

17. The method of claim 14, wherein the therapeutically effective amount ranges from 0.1 to 10 ppm.

18. The method of claim 14, wherein said gas comprises less than 5 ppm NO2.

19. The method of claim 14, wherein said gas comprises less than 25 ppm NO.

20. A method of reversibly modifying duodenal motility and contractile activity of the sphincter of Oddi comprising directly contacting the sphincter of Oddi with a gaseous composition comprising a homogenous blend of nitrogen and ethyl nitrite in a therapeutically effective amount, wherein said gaseous composition comprises less than 48 ppmv ethanol, wherein the gaseous composition is delivered to the gastrointestinal tract of the subject.

* * * * *